US011366120B2

(12) United States Patent
Gao et al.

(10) Patent No.: US 11,366,120 B2
(45) Date of Patent: Jun. 21, 2022

(54) PEPTIDE CAPTURE AND CHARACTERIZATION

(76) Inventors: Xiaolian Gao, Houston, TX (US); Xiaochuan Zhou, Houston, TX (US)

(*) Notice: Subject to any disclaimer, the term of this patent is extended or adjusted under 35 U.S.C. 154(b) by 2678 days.

(21) Appl. No.: 13/261,787

(22) PCT Filed: Jun. 8, 2012
(Under 37 CFR 1.47)

(86) PCT No.: PCT/US2012/000281
§ 371 (c)(1),
(2), (4) Date: Jan. 28, 2015

(87) PCT Pub. No.: WO2012/170078
PCT Pub. Date: Dec. 13, 2012

(65) Prior Publication Data
US 2021/0318328 A1  Oct. 14, 2021

Related U.S. Application Data

(60) Provisional application No. 61/520,306, filed on Jun. 8, 2011.

(51) Int. Cl.
*G01N 33/68* (2006.01)
*B01L 3/00* (2006.01)
*G01N 33/574* (2006.01)

(52) U.S. Cl.
CPC ........ *G01N 33/6842* (2013.01); *B01L 3/5027* (2013.01); *G01N 33/574* (2013.01); *B01L 2300/0816* (2013.01); *B01L 2300/0819* (2013.01)

(58) Field of Classification Search
CPC ............. G01N 33/6842; G01N 33/574; G01N 33/573; G01N 2035/00158; B01L 3/5027; B01L 2300/0816; B01L 2300/0819
USPC .......... 436/501, 64, 813; 422/502, 504, 507; 435/330, 7.23
See application file for complete search history.

(56) References Cited

U.S. PATENT DOCUMENTS

2010/0173797 A1*  7/2010  Jacobs ................ B01J 19/0046
506/9

OTHER PUBLICATIONS

Shigaki S, Yamaji T, Han X, Yamanouchi G, Sonoda T, Okitsu O, Mori T, Niidome T, Katayama Y. A peptide microarray for the detection of protein kinase activity in cell lysate. Anal Sci. Mar. 2007;23(3):271-5. doi: 10.2116/analsci.23.271. PMID: 17372367 (Year: 2007).*
Schutkowski et al. (Schutkowski M, Reineke U, Reimer U. Peptide arrays for kinase profiling. Chembiochem. Mar. 2005; 6(3):513-21. doi: 10.1002/cbic.200400314. PMID: 15742386 (Year: 2005).*
Min DH, Mrksich M. Peptide arrays: towards routine implementation. Curr Opin Chem Biol. Oct. 2004;8(5):554-8. doi: 10.1016/j.cbpa.2004.08.007. PMID: 15450500 (Year: 2004).*

(Continued)

*Primary Examiner* — Christopher L Chin
*Assistant Examiner* — Mohammad Ali Al-Ameen
(74) *Attorney, Agent, or Firm* — G. Kenneth Smith

(57) ABSTRACT

The invention relates to the measurement and profiling of proteins including phosphoproteins from cells in particular the measurement and profiling of phosphoproteins involved in cancer.

1 Claim, 18 Drawing Sheets

(56) References Cited

OTHER PUBLICATIONS

Arend Sikkema, Sander Diks, Wilfred F.A. den Dunnen, Arja ter Elst, Frank J.G. Scherpen, Eelco W. Hoving, Rob Ruijtenbeek, Piet J. Boender, Rik de Wijn, Willem A. Kamps, Maikel P. Peppelenbosch and Eveline S.J.M. de Bont. Cancer Res Jul. 15, 2009 (69)(14) 5987-5995; DOI: 10.1158/0008-5472.CAN-08-3660) (Year: 2009).*

Thiele A, Weiwad M, Zerweck J, Fischer G, Schutkowski M. High density peptide microarrays for proteome-wide fingerprinting of kinase activities in cell lysates. Methods Mol Biol. 2010;669:173-81. doi: 10.1007/978-1-60761-845-4_14. PMID: 20857366 (Year: 2010).*

* cited by examiner

FIGURE 2

| SH2 proteins | #AA | MW | Function | Motif* |
|---|---|---|---|---|
| ZAP-70 | 619 | 70KD | Kinase | |
| Grb2 | 217 | 25KD | Adaptor | |
| BTK | 659 | 76KD | Kinase | |
| Src | 536 | 60KD | Kinase | |

FIGURE 3

| Cell line | gene cluster | ER | PR | P53 | Cell type | Culture Medium |
|---|---|---|---|---|---|---|
| MCF10A | basal B | - | - | $+/-^{WT}$ | Normal mammary epithelium | DMEM/F12 |
| MCF7 | luminal | + | + | $+/-^{WT}$ | invasion ductal carcinoma | DMEM, 10%FBS |
| MDA-MB231 | basal B | - | - | $++^{WT}$ | adenocarcinoma | DMEM, 10%FBS |
| T47D | luminal | + | + | $++^{WT}$ | invasion ductal carcinoma | RPMI, 10%FBS |

FIGURE 8

| Phosphomotifs interacting with GRB2 | Sequence (N' to C') | Swiss prot ID | Reported Protein interactions | Reference |
|---|---|---|---|---|
| CSF3R_787 | yENLWF | Q99062 | SYK,SH3BP2 | Hunter MG, et al. (2004), de Koning JP, et al. (1996) |
| DYST_999 | yQNVLT | Q03001 | GRB2 | not reported |
| EPOR_489 | yENSLI | P19235 | LYN,SH3BP2, | Sulahian R, Cleaver O, Huang LJ (2009) |
| ETV6_314 | yMNHIM | P41212 | GRB2 | Million, RP et al 2004 |
| FAK1_925 | yENVTG | Q05397 | SRC,STAT3,SHC1,GRB | Mitra SK, et al. (2006), Kaneda T, et al. (2008) |
| FLT1_1213 | yVNAFK | P17948 | PTPN11,GRB2,NCK1,P | Ito N et al (1998, 2001) |
| FLT3_768 | yENQKR | P36888 | GRB2 | Masson K, et al. (2009) |
| FLT3_955 | yQNVDG | P36888 | GRB2 | Masson K, et al. (2009) |
| FLT3_969 | yQNRRP | P36888 | GRB2 | Masson K, et al. (2009) |
| FRS2_196 | yVNTTG | Q8WU20 | GRB2 | Hadari YR et al (1998) |
| GSTP1_199 | yVNLPI | P09211 | GRB2 | Okamura T, et al. (2009) |
| IRS1_47 | yENEKK | P35568 | GRB2,SH3BP2 | not reported |
| LAT_200 | yVNVPE | O43561 | GRAP2,GRAP,VAV1,PL | Zhang W, et al. (1998, 2000), Malbec O, et al. (2004) |
| LAT_220 | yVNVSQ | O43561 | VAV1,GRB2,PLCG1,GR | Malbec O, et al. (2004) |
| LAX1_268 | yVNMTG | Q8IWV1 | GRB2,PIK3R1 | not reported |
| LAX1_294 | yENVPA | Q8IWV1 | GRB2 | not reported |
| LAX1_373 | yENVLT | Q8IWV1 | GRB2 | Mayya V, et al. (2009) |
| NFAM1_220 | yTALQR | Q8NET5 | SYK,ZAP70 | Yang J, et al (2003), Ohtsuka M et al. (2004) |
| NTAL_136 | yQNFSK | Q9GZY6 | GRB2 | Iwaki S, et al. (2008) |
| NTAL_95 | yENVLI | Q9GZY6 | GRB2 | Iwaki S, et al. (2008) |
| PDGFRB_716 | ySNALP | P09619 | GRB2,GRB7 | Arvidsson AK, et al. (1994) |
| PILRA_246 | yENIRN | Q9UKJ1 | PTPN11, PTPN6 | not reported |
| PTPN11_279 | yKNILP | Q06124 | GRB2 | Mitra S, et al (2008) |
| PTPN11_546 | yTNIKY | Q06124 | PTPN11,GRB2,FYN,SO | Bennett AM, et al. (1994) |
| PTPN11_584 | yENVGL | Q06124 | PTPN11,GRB2,FYN | Araki T et al (2003) |
| PTPRA_798 | yANFK | P18433 | SRC,GRB2 | Hao Q et al (2006); Chen M et al (2006) |
| SHC1_427 | yVNIQN | P29353 | GRB2 | Ursini-Siegel J, et al. (2008); Patrussi L, et al. (2005) |
| SHIP1_556 | yMNILR | Q92835 | GRB2,INPP5D | CST curated data |
| SOS1_974 | yQNQPY | Q07889 | GRB2 | not reproted |
| SPTAN1_2430 | yQNLTR | Q13813 | GRB2 | Pighi C, et al. (2011), Rikova K, et al. (2007) |
| TNFL6_258 | yVNVSE | P48023 | GRB2 | not reported |
| XPO7_669 | yTALGR | Q9UIA9 | PTPN11,PTPN6 | not reported |

FIGURE 11

| SH2 domain protein | Our study | Previous studies | Ref |
|---|---|---|---|
| GRB2 | pY-E/V/Q/K-N-V/I/L | pY-E/Q-N-A/V/I/L/M/F/Y/W | Kessels et al 2002 |
| SRC | pY-E/S/A/T-E/T/I/S-L/I/V-D/V-F/L | pY-E/D/T-E/N/Y-L/I | Huang et al 2008 |
| BTK | pY-A/E/S-D/M/L/I-N/E/V/D-L/V/P/I/M | pY-E/D/M/L/I-E/D/I-I/P/M/L | Tzeng et al 2000 |
| ZAP70 | pY-S/A/T-S/A/F/T-L | pY-E-N-V/L-D | Huang et al 2008 |

FIGURE 12

| SH2 domain | PPEP_Seq | PPEP_Pro | Pho_site | Description |
|---|---|---|---|---|
| Grb2 | yENVPA | LAX1 | 204 | lymphocyte transmembrane adaptor 1 |
| | yIIANI | PTPN11 | 304 | protein tyrosine phosphatase, non-receptor type 11 |
| | yQIILTR | SPTAN1 | 2430 | spectrin, alpha, non-erythrocytic 1 (alpha-fodrin) |
| | yQNSAS | LAT2 | 193 | linker for activation of T cells family, member 2 |
| | yQNVLT | DST | 633 | dystonin |
| | vNIQN | SHC1 | 313 | SHC (Src homology 2 domain containing) transforming protein 1 |

Strength of GRB2 interaction

⟵⟶ Weak
⟵⟶ Medium
⟵⟶ Strong
⟵⟶ Strongest

FIGURE 15
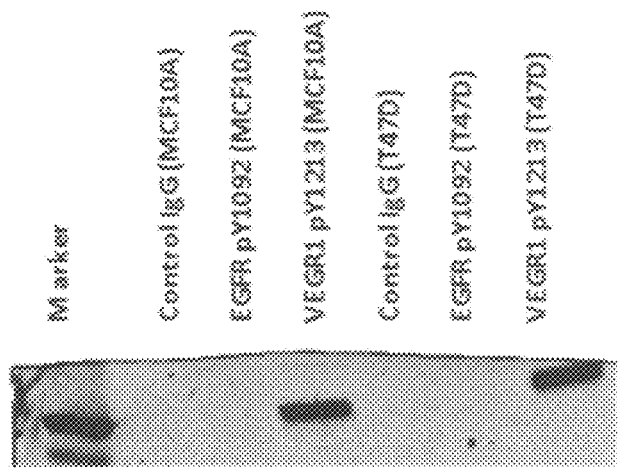
Immunoprecipitation of VEGFR1 pY1213 antibody show GRB2 interaction from MCF10A and T47D cells
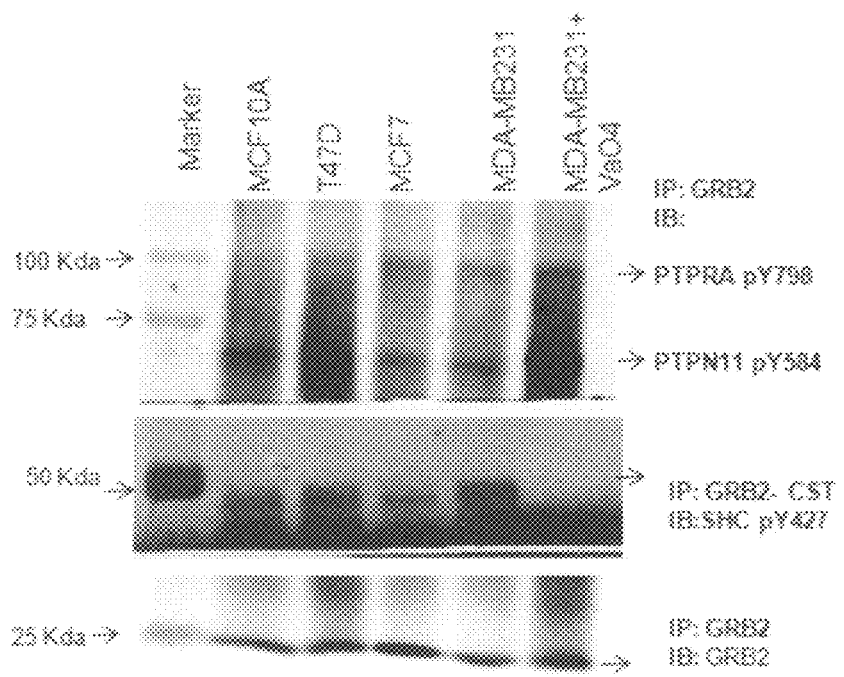

PEPTIDE CAPTURE AND CHARACTERIZATION

RELATED US APPLICATION DATA

This application claims priority to the filing date of PCT/US2012/000281 filed Jun. 8, 2012 which claims priority to U.S. Provisional Application No. 61/520,306 filed Jun. 8, 2011; the disclosures of which are incorporated by reference.

FIELD OF THE INVENTION

The invention relates to the measurement and profiling of proteins including phosphoproteins from organisms in particular the measurement and profiling of phosphoproteins involved in cancer.

BACKGROUND OF THE INVENTION

The fundamental role of proteins acting in the context of network and location is well-established. There has been explosive growth in the knowledge of diverse protein functions and protein-protein interactions as a form of communication in an intra- and inter-cellular environment. It is imperative to take full advantage of this sea of information and develop measures and means to practically benefit human life, for instance, to achieve cancer treatment with higher rate of success, or even curing the disease. To do so, detection and profiling proteins in proteomes for the large populations is essential. However, this goal has not been achieved today.

Presently, proteomics tools include protein mass spectrometry coupled with protein separation methods, such as 2D electrophoresis, immunoprecipation, immunoaffinity binding, liquid chromatography, random peptide-based bead binding. Additionally, protein/antibody microarray and peptide microarray have found limited applications. Due to the limitations of these methods which are detailed in numerous literature publications, for the ~20,000 basic forms of proteins and potentially 100,000 or more variants of proteins in any given cell types and at any moment, only one tenth or far less can be monitored. The measurements further suffer from low sensitivity and limited range in quantities of proteins (i.e. dynamic range). The lack of knowledge of a large number of proteins has greatly hindered progress, and intensive effort has continuously been invested in the field.

The human kinome has more than 500 protein kinase proteins, which does not include isoforms, splicing isomers, and the various post-translational modified proteins. Thousands of amino acid phosphorylation sites simultaneously exist in cellular proteins and the specific information about this prophosproteome contains rich information for basic cellular activities and for human health Protein kinases are defined by their ability to catalyze the transfer of the terminal phosphate of ATP to substrates that usually contain a serine, threonine or a tyrosine residue. These kinases typically share a conserved arrangement of secondary structural elements that are arranged into 12 subdomains that fold into a bi-lobed catalytic core structure with ATP binding into a deep cleft located between the lobes. Deregulation of kinase activity is a major mechanism by which cancer cells evade normal physiological constraints on growth and survival. Deregulation of kinase function has also been implicated in other disorders including immunological, neurological, metabolic and infectious disease. Thus, kinase inhibitors have been and are being developed to treat a variety of diseases including cancer.

Therefore, there exists a need for efficient, repeatable and inexpensive methods and devices for measuring proteins including phosphoproteins from cells, blood, serum, other fluids and/or tumors and characterizing those proteins.

SUMMARY OF THE INVENTION

The present invention relates to methods for detecting phosphoproteins on peptide microarrays. The phosphoproteins in cells derived from any tissue including but not limited to blood or serum or tumor or tissue may be detected by making a microarray containing peptides that bind phosphoproteins, lysing cells and collecting the proteins from the cells, putting the proteins in contact with the peptides of the microarray and detecting the proteins including the phosphoproteins.

The present invention relates to methods for differential detection of phosphoprotein expression in cancerous and non-cancerous cells. The differential expression of the phosphoproteins in cancerous and non-cancerous cells may be determined by making a microarray containing peptides that bind phosphoproteins and lysing the cancerous cells and collecting proteins from the cells and the putting the proteins in contact with the peptides of the microarray and detecting the phosphoproteins from the cancerous cells. The same method can be used for non-cancerous cells: lysing the non-cancerous cells, collecting proteins from these cells and covering the microarray with the proteins and detecting the phosphoproteins from the non-cancerous cells and comparing the relative expression of these proteins in cancerous and non-cancerous cells.

The present invention relates to methods for differential detection of phosphoprotein expression in treated cancerous cells and untreated cancerous cells. The differential expression of the phosphoproteins in treated cancerous cells and untreated cancerous cells may be determined by making a microarray containing peptides that bind phosphoproteins and lysing the treated cancerous cells and collecting proteins from the cells and the covering the microarray with the proteins and detecting the phosphoproteins from the treated cancerous cells. The same method can be used for untreated cancerous cells, lysing the untreated cancerous cells, collecting proteins from these cells and the covering the microarray with the proteins and detecting the phosphoproteins from the untreated cancerous cells and comparing the relative expression of these proteins in treated cancerous and untreated cancerous cells.

The present invention relates to methods for differential detection of phosphoprotein expression in cancer cells treated with a kinase inhibitor and untreated cancerous cells. The differential expression of the phosphoproteins in cancer cells treated with a kinase inhibitor and untreated cancerous cells may be determined by making a microarray containing peptides that bind phosphoproteins and lysing the cancer cells treated with a kinase inhibitor and collecting proteins from the cells and the covering the microarray with the proteins and detecting the phosphoproteins from the kinase inhibitor treated cancer cells. The same method can be used for untreated cancerous cells (lysing the untreated cancerous cells, collecting proteins from these cells and the covering the microarray with the proteins and detecting the phosphoproteins from the untreated cancerous cells and comparing the relative expression of these proteins in kinase inhibitor treated cancer cells and untreated cancerous cells.

The present invention relates to peptide microarrays containing peptides which bind proteins including phosphoproteins.

The present invention relates to microfluidic arrays containing peptides which bind phosphoproteins.

The present invention relates to methods of determining phosphorylation patterns in diseased cells such as cancer cells.

The present invention relates to microarrays containing particular sets of peptides to detect phosphoroproteins.

The present invention relates to detecting phosphoproteins in cells on microarrays in which Grb2 is used as a reporter for detection of the phosphoproteins.

The present invention relates to methods of binding proteins including phosphoproteins to a microarray and then releasing the proteins to be analyzed by other method including mass spectroscopy.

DESCRIPTION OF THE FIGURES

FIG. 2—Graphical representation and listing of SH2 binding proteins.

FIG. 3—List of cancer cell lines for profiling.

FIG. 8—Examples of phosphomotif-Grb2 interactions observed on PPEP array.

FIG. 11—GRB2 SH2 domain the binding motif the consensus of phosphopeptides is pY-E/V/Q/K-N-V/I/L.

FIG. 12—List of signature peptides for Grb2 SH2 domain.

FIG. 15—Western blot of signature GRB2~Phosphoprotein complexes from Breast cancer cells. The western blot analyses demonstrate the direct GRB2 mediated and the indirect (non-GRB2 mediated) interactions observed on the phosphopeptide microarray.

DETAILED DESCRIPTION OF THE INVENTION

Figure 1:
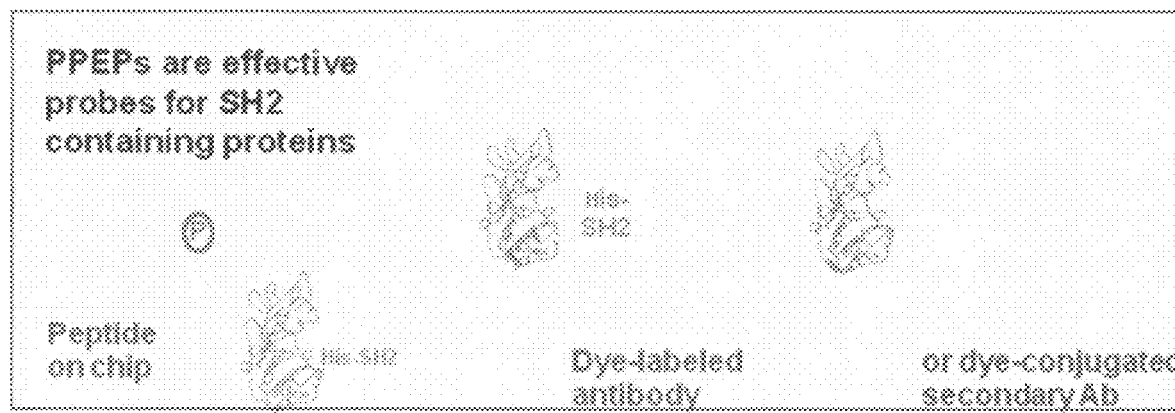
FIG. 1—Graphical representation of binding of Grb2 to SH domain and use of reporter Abs.
Figure 4:
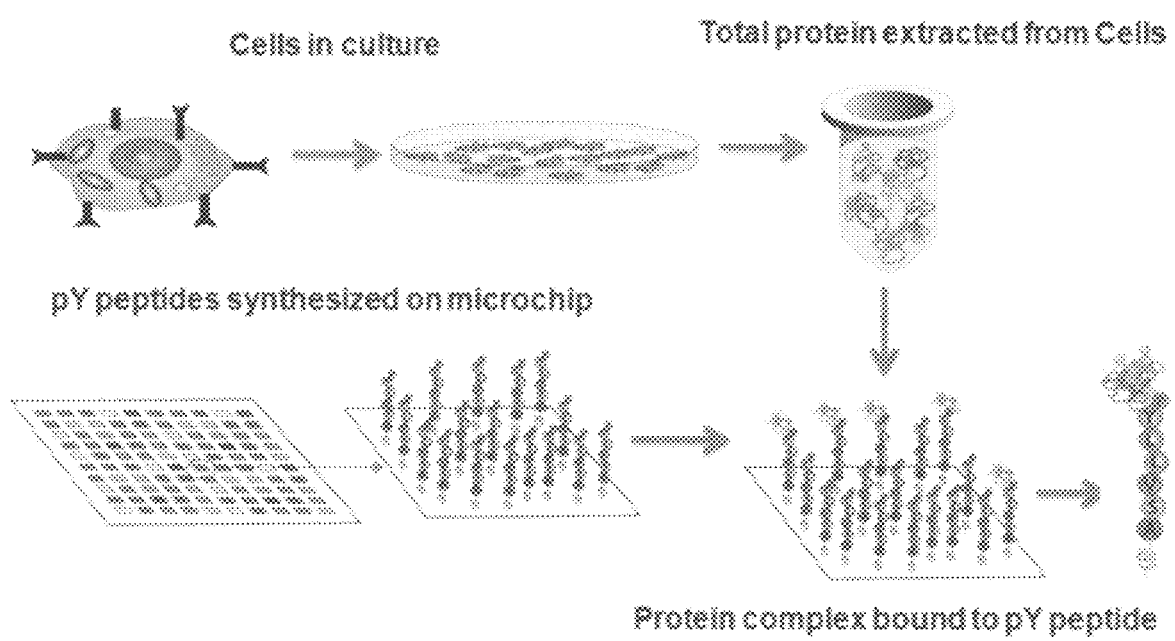
FIG. 4—Diagram of phosphopeptide binding of protein complexes in cells.
Figure 5:
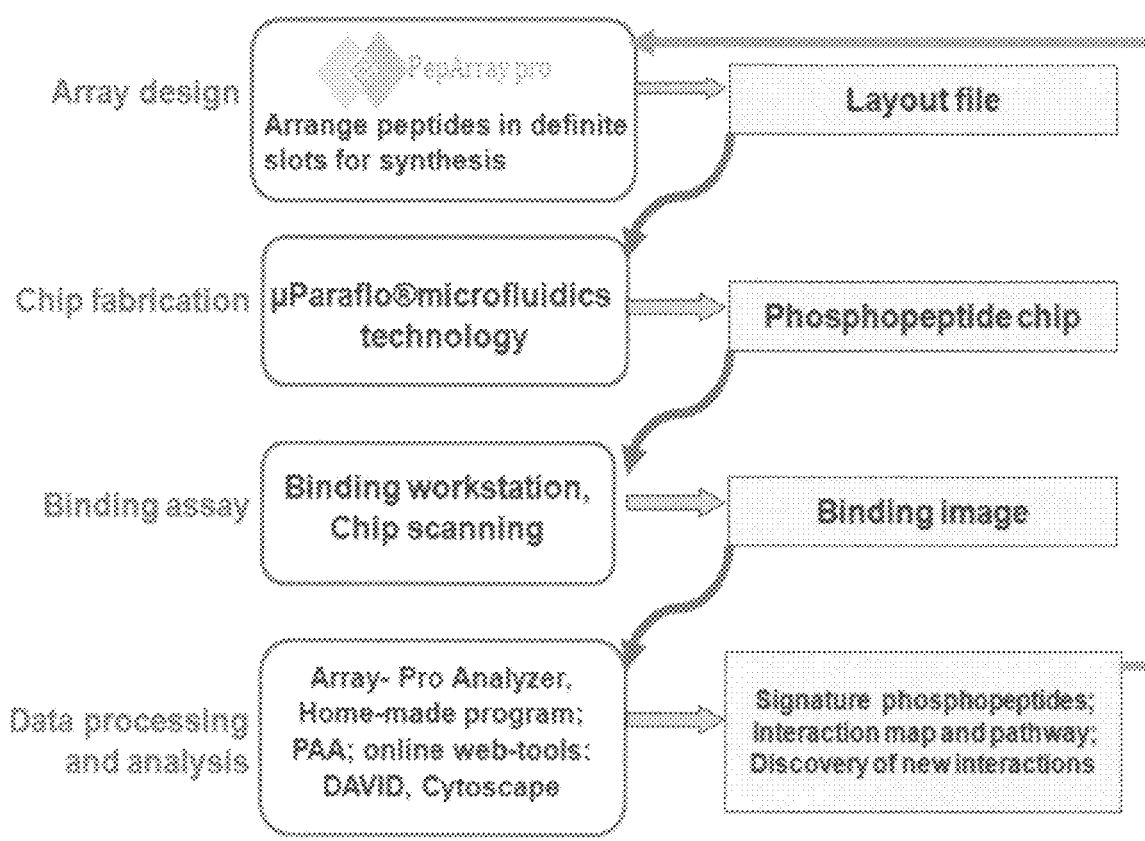
FIG. 5—Diagram of phosphoprotein profiling

Protein structural domain binding to specific substrate peptides underlies protein-protein interactions has been well-established. Rationales for protein capture based on protein domain resignation by peptide binding include: (a) cancers are associated with significant changes in expression levels for many proteins, including the expression levels of many signaling and regulatory proteins. (b) signaling and regulatory proteins often contain one or multiple, peptide binding domain(s), such as those specific for SH3 (Src homology domain 3) (approximate 300 domains in human) in oncogenes SRC or PH (Pleckstrin homology domain) (more than 250 domains in human) in protein kinases AKTs, PKCs, in receptor IRS-1, small G-protein Ras-GRF, etc., and ANK repeats (ankyrin repeats) (more than 12 families of ANK repeats in transmembrane domains as adapters) for protein-protein interactions to mainly maintain the integrity of the cell membrane. ANKs are found in many signaling and interactive proteins such as SOCS box protein 8, NF-kappa-B inhibitor alpha and beta. ANK repeats are also found in human-invading virus. The ANK repeats have unique structures which have been used as template for designing protein binding ligands. The binders of these domains are contained in several hundreds of human proteins and their binding interactions are likely to have signatures due to their different peptide binding domains. (c) immobilized peptides are able to show specific binding recognitions for peptide binding proteins. It is therefore of great interest to use a systems biology approach to explore domain recognition as a means to quantitatively detect proteins, and to profile domain binding to substrate sequences at a proteomic scale. Integrated methods for microarray and mass spec experiments and computational modeling have the potential to broaden the range of protein measurements in cancer samples. Since CMPT profiles proteins through differential binding to multiple signature peptides it increases detection of low abundant proteins.

Phosphoprotein binding domains (PPBDs), which consist of conserved amino acid sequences, or conserved structural motifs, or both, are found in many signaling and regulatory proteins. These motifs confer affinity, and, typically, specificity to a substrate protein. Table B1 lists 11 representative PPBD domains (14-3-3, BRCT, C2, FHA, LRR, MH2, PPBD (PIK1, etc.), PTB, SH2, WD-40, WW). Each family of domains can be divided into multiple groups having different binding affinities to pY- or pS/pT-phosphorylation sites or both. Mutations, deletions, or altered-expression of PPBDs can directly interfere with protein-protein interactions; thus, changes in the expression levels of PPBD-containing proteins can be important biomarkers in cancers. For example, SRC, which contains an SH2 domain, is a proto-oncogene that is normally sequestered in an inactive conformation via an intramolecular binding of pY530 to its SH2 domain. A mutation in a residue in this SH2 domain that leads to its reduced binding to a substrate, and increased tyrosine kinase activity for SRC, has been found in breast (Aebersold, R., Goodlett, D. R. (2001) Mass spectrometry in proteomics. Chem. Rev. 101(2):269-95 Aebersold, R., Goodlett, D. R. (2001) and colon cancers (Yates, J. R., 3rd, Eng, J. K., McCormack, A. L., Schieltz, D. (1995) Method to correlate tandem mass spectra of modified peptides to amino acid sequences in the protein database. Anal Chem 67, 1426-1436). In an additional example, WWOX, which contains a WW domain and encoded by a putative tumor suppressor gene, is located at a chromosome region (16q23.3-q24.1) that is commonly affected by allelic losses in breast cancers (Schwartz, J. C., Senko, M. W., Syka, J. E. (2002) A two-dimensional quadrupole ion trap mass spectrometer. J. Am. Soc. Mass Spec. 13, 659-669); this protein has been implicated in multiple tumor types (Perkins, D. N., Pappin, D. J., Creasy, D. M., Cottrell, J. S. (1999) Probability-based protein identification by searching sequence databases using mass spectrometry data. Electrophoresis 20, 3551-3567). Furthermore, the suppression of the expression of the tumor suppressor protein 14-3-3σ, which contains the pS/pT-binding domain 14-3-3, has been associated with multitude of human epithelia cancers, including lung carcinomas, bladder carcinomas, hepatocellular carcinomas, oral carcinomas, and head-and-neck squamous cell carcinomas (Gong, W., Zhou, D., Ren, Y., Wang, Y., Zuo, Z., Shen, Y., Xiao, F., Zhu, Q., Hong, A., Zhou, Z., Gao, X., and Li, T. (2008) PepCyber P~PEP: A database of human protein-protein interactions mediated by phosphoprotein binding domains. Nucleic Acids Res. 36, D679-D683).

Signaling cascades mediated by protein phosphorylation are achieved through recruitment of substrate molecules by PPBDs via specific recognition of distinct PPEP sequences (Nuhse, T. S., Stensballe, A., Jensen, O. N. & Peck, S. C. (2003) Large-scale analysis of in vivo phosphorylated membrane proteins by immobilized metal ion affinity chromatography and mass spectrometry. Mol. Cell Proteomics 2, 1234-1243). PPBDs have been classified into a variety of families each family has subfamilies and isoforms that have distinct substrate-recognition properties. For instance, more than 100 human SH2 domains, possessing distinct binding properties, have been identified. Some proteins contain multiple PPBD or PPBD/non-PPBD domains, such as the tandem SH2 contained in SHP2, which is a cytoplasmic phosphatase and has been implicated in multiple signaling pathways, including the RAS/MAPK pathway; recently, this protein has been associated with myeloid malignancy, the PTB (phosphotyrosine-binding) and SH2-containing SHC is an adapter protein that has been implicated in the SOS-Grb2-RAS-MAPK signaling cascade, which is active during cellular proliferation, differentiation and apoptosis. Table B1 exemplifies PPBDs' involvement in eight GO (the Gene Ontology) cell cycle pathways and GO also provides information on the related PPBD domain-carrying proteins. These using, for instance, ELISA sandwich assays, isothermal calorimetric measurements, nuclear magnetic resonance spectroscopy, x-ray methods and array binding methods.

Figure 16:
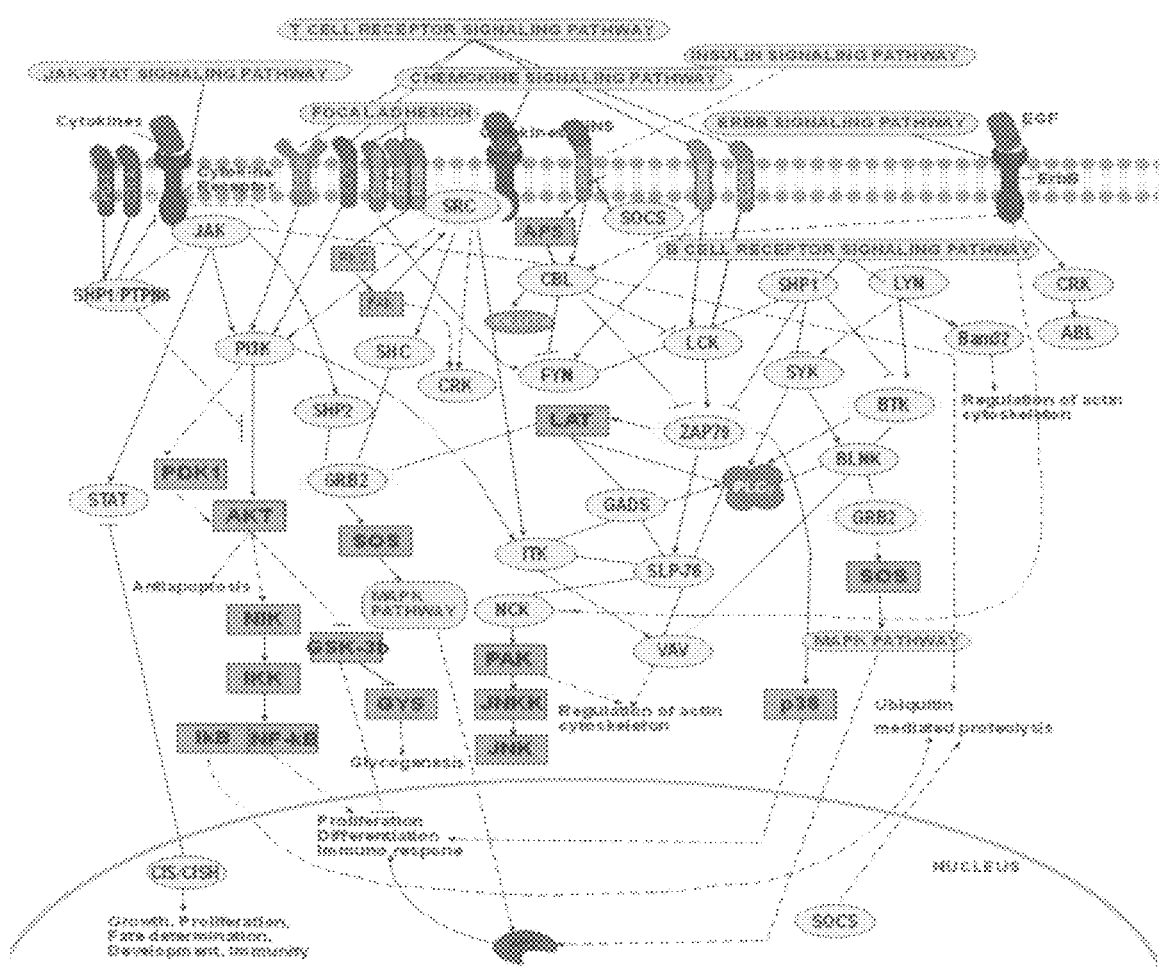
FIG. 16—Diagram of SH protein network.

SH2 is a family of pY-phosphopeptide binding domains (pY-PPEPs) which has significant value for protein profiling. More than one hundred SH2 domains have been identified in human proteins, including well-known cell receptor or cytoplasmic tyrosine kinases, other types of kinases, and a number of phosphatases, adapters, and scaffold proteins. pY-PPEP-SH2 interactions are key regulatory elements of cellular biological activities, and SH2 domains are the most widely studied in domain-based protein-protein interactions. SH2 domains contain a binding site along with conserved sequence regions, which modulate its function by maintaining native folding and sequence selectivity for binding. A large number of in vitro studies of SH2 and SH2-binding complexes have generated a wealth of information on the structures, in vitro binding properties, energies, sequence-specificities, and computational predictions, for SH2 domains. Information on peptide-SH2 systems has been compiled in a number of databases. In other studies, the binding of tandem SH2 domains, such as those found in SHP2, Syk, and ZAP-70, show SH2 domains are modular units that act independently in binding. For instance, an ITAM peptide (pYXX(I/L)X$_{6-8}$pY) can simultaneously occupy these tandem SH2 domains. These results have clearly established a broad spectrum of specificities for interactions of peptide sequences with SH2 domains. SH2 proteins of interest include but are not limited to SHP2-NSH2 (the SH2 at the N-terminal of the phosphatase protein), SHP2-CSH2, SHP2-NSH2-CSH2, PI3K (p85α) CSH2, SRC-SH2, Stat3-SH2), His-Yes, GST-PLC gamma SH2, GST-p85a SH2, GST-Grb-2 SH2). FIG. 16 shows a diagram of an SH2 protein network. The PPEP array estab-

TABLE B1

Information about the Phosphoproten Binding Domains (PPBDs)[1]

| Domain | # (est.) hs Protein | pY | pS/pT | Binding Consensus (Examples) | A[2] | B | C | D | E | F | G | H |
|---|---|---|---|---|---|---|---|---|---|---|---|---|
| 14-3-3 | >9 | | v | RSXpSXP (14-3-3s); RX(Y/F)XpSXP (14-3-3s | 4 | 0 | 2 | 0 | 0 | 0 | 1 | 2 |
| BRCT | 23 | | v | p(S/T)XXF (PTIP) | 6 | 11 | 2 | 0 | 0 | 0 | 0 | 0 |
| C2 | 120 | v | | (PKCδ) | 2 | 1 | 5 | 0 | 2 | 0 | 1 | 3 |
| FHA | 26 | | v | pTXXD (Rad53-FHA1) | 7 | 4 | 0 | 0 | 0 | 0 | 2 | 3 |
| LRR | 233 | | v | (β-TrCP) | 2 | 0 | 10 | 0 | 0 | 0 | 17 | 10 |
| MH2 | 3 | | v | SpSXpS (R-Smad) | 0 | 0 | 0 | 0 | 0 | 0 | 0 | 1 |
| PBD | 18 | | v | SpT (Plk1) | 3 | 0 | 0 | 0 | 0 | 0 | 0 | 0 |
| PTB | 44 | v | | NPXpY (Shc, IRS) | 5 | 0 | 1 | 0 | 3 | 0 | 2 | 3 |
| SH2 | 109 | v | | pYXX(I/P) (Crk); pY(I/V/L)X(I/V/L) (SHP2); pY(M/I/L/V/E)XM (p85α); etc. | 9 | 1 | 9 | 12 | 3 | 0 | 2 | 6 |
| WD-40 | 267 | | v | (Apaf-1) | 13 | 6 | 2 | 0 | 1 | 8 | 1 | 3 |
| WW | 49 | | v | PPXY (YAP65); PPLP (FE65); PGM (FBPs); pSP, pTP (Pin); PR (FBP30) | 6 | 1 | 2 | 0 | 0 | 0 | 1 | 5 |

[1]Source of Information includes Phospho. ELM, ELM and literature discussed in this application.
[2]Pathway GO terms for a PPBD. A GO term may occur in different pathways, giving more than one count for a protein.
A—Cell cycle GO:0007049;
B—DNA Repair GO:0006281;
C—Apoptosis GO:0006915;
D—JAK-STAT cascade GO:0007259;
E—MPKKK cascade GO:0000165;
F—Wnt pathway GO:0016055;
G—Cell adhesion GO:0007155;
H—Cell differentiation GO:0030154 example pathways and proteins illustrate their association with tumorgenesis and cancers. In most cases, PPEP-PPBD complexes are stable enough to be detected experimentally, lishes a probe-target platform for analysis of proteins in cell. Tyrosine phosphorylation is the hallmark of activation of Receptor Tyrosine Kinase (RTK) pathway proteins which regulate various aspects of cellular division, multiplication, differentiation and apoptosis. Temporal and spatial misregulation of RTKs leads to various cancers. Phospho-protein enrichment coupled with high-throughput mass spectrometry methods have lead to cataloguing of thousands of such tyrosine phospho modifications on proteins and is still expanding rapidly Comprehensive maps of protein networks regulated by such phospho-motifs lead to identification of nodal signaling protein motifs and open up avenues for better therapeutic intervention strategies. Using a set of breast cancer cells a detailed map of interaction between phospho-motifs representing various RTK pathway proteins and an RTK adaptor protein GRB2 has been generated. Several novel interactions of tyrosine phospho-motifs with GRB2 in breast cancer cell systems have been determined using the methods and devices of the present invention.

Microarray design involves creating a list of phosphopeptides (SH2-containing protein binders), negative controls, synthesis quality control peptides, etc. The pepchip in this application emphasizes the inclusion of phosphopeptides for complete coverage of the SH2 target proteins. Peptides are selected from the database PepCyber P~PEP (phosphopeptide). More than seven thousand phosphorylation sites and binding protein interactions have been compiled from: (a) Mining general protein databases including Swiss-Prot and NCBI Genbank to extract protein entries with the binding domains (such as SH2 domains). For each of the extracted phosphor-binding protein (PPBD) proteins, GO terms (molecular function and biological process) was annotated to enable downstream data analysis linking to protein biology, (b) Mining protein interaction databases including BIND, HPRD and DIP to extract PPEP interactive proteins. In particular, the PPBD proteins involved in important signaling pathways, such as RAS/MAPK responsible for malignant cell growth and proliferation, JAK/STAT associated with cytokines, lymphokines, and growth factors signals and also cancer, EGFR/SRC associated with activation of tumorgenesis, etc. (c) Mining protein domain databases, including PDB, Pfam (and other component databases of Interpro) to extract domain proteins through motif search and also extract peptide substrates. (d) Mining short peptide motif databases, including ELM, Phospho.ELM, and PhosphoSite to extract PPEPs and focus on the interactions of the peptides with protein domains. Peptides involved in important signal transduction pathways, such as those which are phosphorylated at tyrosine residues to become substrates of the SH2 domains are of particular interest. (e) Literature search through PubMed, where a number of recent publications using computation, 2D electrophoresis gel and mass spectrometry techniques to survey phosphorylation sites in proteins and the peptide scanning array results provide rich information on PPEP sequences (thousands of such sequences have been reported. This information has been supplemented with the host protein information.

The peptide microarrays (chips) can be synthesized in a variety of formats including a 4 k chip which contains 3,968 pico-liter reaction chambers (128 rows and 31 columns) with one kind of peptide made in each chamber. Inside the chamber, peptides are directly synthesized on the surfaces of the chamber; each reaction chamber can generate close to 1 fmol of peptide. Another chip format can have 30,132 reaction chambers (30 k chip, 162 rows and 31×6 columns (six sets of reaction chambers)). The basic working principles are the same for the both chips but the overall surface of the reaction chambers is smaller in the 30 k chip. About 0.2 fmol of peptides are made in each chamber for the 30 k chip. The reaction volume of a chamber is 200 pL and the total volume of the chip is about 10 µL from inlet to outlet for the 4 k chip. If the SH2 binding occupies ½ of the available phosphopeptides in a reaction chamber and then the total proteins recovered from the 4 k chip would be 3,968×0.5 fmol, i.e. about 2 pmol in total of about 4,000 proteins. Multiple reaction sites containing the same peptide can be synthesized since 4,000 or more (there will be sites which would bind to more than one proteins) proteins is more than a one run Mass analysis capacity.

The microarrays may include microfluidic chips which may have channels, reaction chambers, and through-holes which can be patterned using an STS etching system in a deep RIE (reactive ion etching) patterning process. The silicon surface inside each reaction chamber may be coated with a thin $SiO_2$ layer (~2,000 Å) using a high-temperature oxidation process so as to enable surface derivatization using silane chemistry. An anodically bonded glass plate (Corning 7740) to the silicon substrate may be used to cover the chip and the glass surfaces may be subsequently derivatized with chemical linkers for use in syntheses. Preferred microarrays are described in US Patent Publication No. 20110143764. A preferred microfluidic reaction device comprises a plurality of chambers having a first conduit and a second conduit a first tapered transport channel having an interior surface the first transport channel being in flow communication with at least one said chamber through connection with said first conduit; and a second tapered transport channel having an interior surface, the second transport channel being in flow communication with at least one chamber through connection with the second conduit, wherein passing a fluid through the microfluidic device provides a volume flow rate across the plurality of chambers which is substantially uniform.

Peptide sequences for use in the microarrays can be obtained from publicly available databases. Target proteins may be sorted according to the pathways in which they participate including the eight major cancer pathways and their major branches. A list of candidate target proteins can be compiled for each pathway. The information about the native substrate peptides of these target proteins (including phosphopeptides that bind PPBD-containing proteins) can be collected from pertinent functional motif databases (PepCyber:PPep, Phospho.ELM, PhosphoSite, PDZbase, MEROPS), protein domain databases (SMART Prosite, Pfam and InterPro), general purpose protein-protein interaction databases (DIP and HPRD), protein structure database (PDB) and the literature. The information can be organized into a pathway-centered database of protein-peptide interactions named PepCyber:PathCap The sequences thereby compiled in the protein binding peptide database reveal high affinity binding preferences (sequence patterns, length, etc. for certain types of target proteins). These analyses will provide in-depth information for improving the coverage of target proteins by capture PepArrays.

The sequences determined to be useful for capturing proteins can then be placed in a layout file, which allows determination of the exact sequence and location (row and column positions) for synthesis. In one chip format, there are 128 rows and 31 columns of reaction sites. The chip design contains replicates, reference, negative and positive sequences so that reliable results can be achieved. Reference sequences of known binding behavior may be included in sub-panels so that they can be used to help to detect signal variation (spot to spot uniformity); Reference spots may also be used to normalize variation within and between chips. Quality control sequences may also be distributed on the chip. In a preferred format the sets are at the same relative position on each chip. Comparison signals may be obtained from QC sequences by direct FAM labeling and by binding of cy3-labeled AFM2 to these constant sequences, to assess synthesis quality and quality of subsequent binding assays. Positive and negative control sequences may be included in the chip format and the control sequences used will depend on type of assays to be performed. For a specific binding assay, the ratio of the binding signals of the positive controls to those of the negative controls may preferably be large. Some designs for SH2-binding peptide arrays will contain an n number of sequences that were originally identified as profiling candidate sequences (parent peptides) using the PepCyber database along with the alanine scanning, mutants (selected residue substitutions), and N-terminal and C-terminal truncation sequences. This diverse group of peptides is synthesized together on a single chip.

One method of synthesizing a peptide array includes: chip design→surface derivatization (attaching alkyl amino silane linker molecules to the chip surface)→anchoring spacer molecules (coupling of chain extension molecules such as oligo ethyleneglycosyl molecules to allow peptides extending away from the surface by at least 30 rotational bonds or by a distance of 3.6 nm. The spacer molecules are densely packed on the surface, providing a non-adhesive layer to reduce non-specific sticking by the assay samples)→deprotection reaction (light activated PGA reaction)→coupling reaction (pY-coupling reaction)→final side chain deprotection. The peptide array synthesis is preferably based on Boc-chemistry, and is carried out on a DNA synthesizer (e.g. Expedite 8909) equipped with an additional module (Genomic Technologies) for accommodation of 20 amino acid-containing bottles, and an optics unit for light irradiation at 405 nm. In a preferred embodiment each array synthesis uses a program to read the sequences to be synthesized and to generate the light irradiation patterns for controlling each step of the deprotection reaction. The reaction cycle comprises deprotection, coupling, and capping steps (Pellois, et al. (2002) Nature Biotechnol.). Optionally, fluorescein may be used in the last coupling step to monitor the synthesis. Synthesis yield is highly reproducible and preferably has a stepwise yield of 90-100% more preferably between 95-100%.

Protein isolated for analysis with the microarrays described above can come from any source in which protein can be isolated. Such sources include but are not limited to cells, blood, serum, tumors and other tissues from which protein can be isolated. In a preferred embodiment cells containing proteins can be washed in cold PBS and lysed in 1-2 mL of lysis buffer containing 20 mM Tris (pH 8), 1% TX-100, 10% glycerol, 137 mM NaCl, 5 mM sodium orthovanadate along with 1% phosphatase inhibitor cocktail and 1% protease inhibitor cocktail (Roche). The cells can be centrifuged to remove the DNA and cellular debris.

Figure 6:
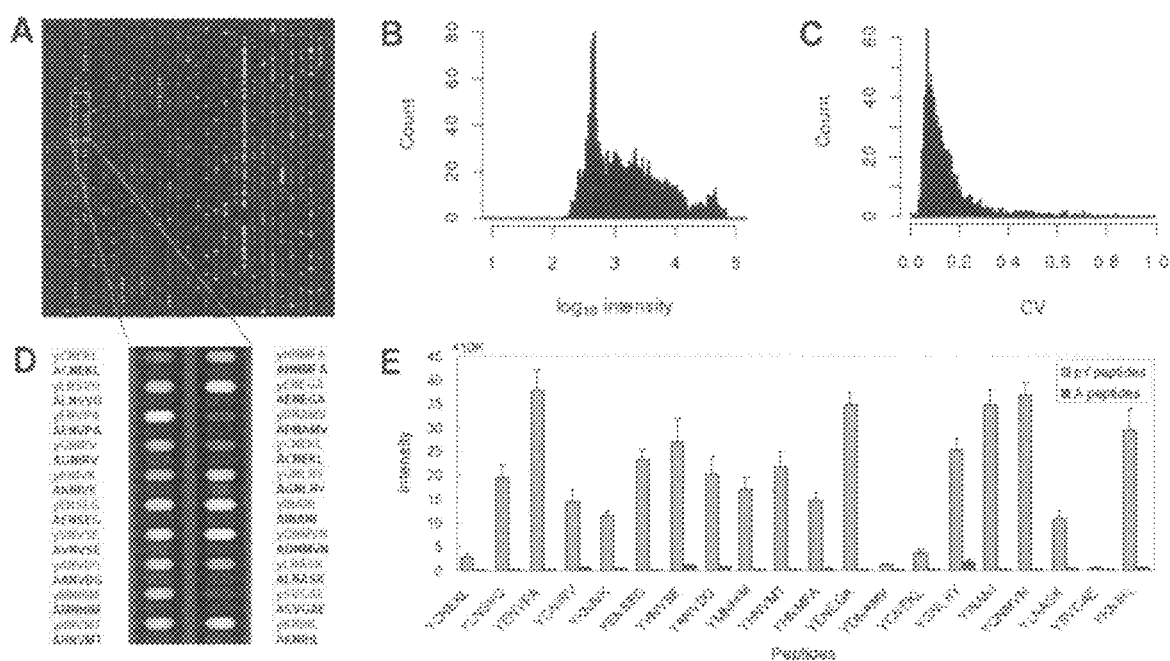
FIG. 6A-E—Analysis of SH2 proteins bound to phosphopeptide microarray.

Proteins can be labeled in a variety of ways. For the SHP2 SH2 domain proteins GST or HIS6 fusion tags can be used. These affinity tags can be detected by using their cognate antibodies on protein bound to peptide sequences on a chip; anti-HIS6 or anti-GST antibodies can be detected using cy3- or cy5-labeled secondary antibodies (cy3-anti-IgG, cy5-anti-IgG). GST tags may have a tendency to cause formation of dimers of the tagged protein, resulting in multivalency enhanced binding; if the protein can be expressed with the HIS6 tag, this potential problem can be avoided. These labeling and detection strategies are applicable to most recombinant proteins containing fusion tag(s); A universal dye labeled anti-IgG conjugate has several advantages including avoidance of cross-binding issues caused by specific antibodies; time and cost savings compared to direct protein labeling, which can cause protein denaturation, and reduction of differences in measurements that may be due to the use of different detection systems. It is also possible to use a two color labeling scheme, where one domain protein can be directly labeled with cy3 and a second domain protein can be stained with cy5-anti-IgG. The two color labeling strategy allows direct comparison of two sets of protein samples of different affinity tags. FIG. 6 shows an array where 3986 peptides were synthesized in situ on a microfluidics based µParaflo® microchip. Among them, 1227 peptides have tyrosine phosphorylated. FIG. 6A shows the binding profile of Grb2 SH2 domain on phosphopeptide array. The array was probed by 500 ng/ml (13 nmol/L) GST-fused Grb2 SH2 domain. The Grb2 binding was detected by 100 ng/ml anti-GST-Hylite 647 conjugate. Signals from proteins bound to phosphopeptides (N-pY-X1-X2-X2-X4-X5-C) compared to respective control peptides (N-A-X1-X2-X2-X4-X5-C) well were scored. FIG. 6B shows the Grb2 binding intensity distribution. Log 10 values were calculated across each intensity. 1847 spots have binding intensities less than 1000, while the binding intensities of 428 spots were more than 10,000. FIG. 6C shows the CV distribution curve Grb2 binding spot. 3695 spots have CVs less than 0.25, showing both peptide synthesis and Grb2 binding are uniform. FIG. 6D is a magnified image of a small region from panel A. Tyrosine phosphorylated peptides (pY peptides) marked with red, while those marked with black control peptides with phosphorylated tyrosine replaced with alanine (A peptides). pY peptides and corresponding A peptides are synthesized in two adjacent positions in the same column. FIG. 6E shows the intensities of Grb2 SH2 domain binding to peptides present in panel D. pY peptides, blue bar, A peptides, brown bar. The Grb2 SH2 domain is able to bind to some pY peptides with intensities anywhere from 5-fold to 30-fold compared to A peptides. Endogenous Grb2 is an excellent reporter for protein or protein complexes. Grb2 binding to PPEP probes can be used to produce differential profiling patterns for many cancer cell lines. For example, upon different tyrosine kinase inhibitor (TKI) drug treatment or differential drug dosage or time, PPEP protein profiling shows different levels of responses. Such information reveals cellular activities, therapeutic responses or sensitivities of therapeutic subjects to drug intervention.

Chip images may be acquired by various techniques. In one embodiment a commercially available microarray scanner (GenPix 4000B, Molecular Device/Axon) can be used to acquire chip images, the Array-Pro Analyzer 4.0 (Media Cybernetics) program to extract signal intensities, and MatrixPro (internal program) for data analysis. Images from anti-IgG staining of arrays can be taken before and after binding and the difference between the two sets of data may be used as binding data. Although normally only a few spots show positive signals with anti-IgG staining, using the signal difference provides a more accurate measurement of the bound protein. This procedure would not be possible with glass slides since scanning causes protein drying on the surface, and the array cannot be reused.

The data may be processed in a MS Excel spreadsheet using a program routine that performs raw signal background subtraction using a local regression method (note that the photolithographically fabricated arrays do not have peripheral areas for background values); data normalization, using a cyclic LOWESS (Locally-weighted Regression) method is used to remove system related variations, such as sample amount variations, dye labeling bias, and signal gain differences between scanners, so that biological relevant variations can be faithfully revealed. Detected signals greater than background plus 3 times the standard deviation can be derived for each color channel; the mean and the co-variance (CV=stdev ×100/replicate mean) of each peptide sequence having a detected signal will be calculated. Those having a CV larger than 30% may not be used in further analyses. For two color experiments, the ratio (log transformed) of the two sets of detected signals, and p-values of the t-test, can be calculated. Differentially detected signals are generally accepted as true when the ratios of the p value is less than 0.01. For clustering analysis of multiple datasets, data adjustment includes data filtering, Log 2 transformation, and gene centering and normalization. Data filtering can be used to remove clustering values from the data set (detected signals or detected ratios that are below a threshold value). Data centering and normalization will transform Log 2 values using the mean and the standard deviation for individual proteins across all samples. Clustering can be performed with a hierarchical method using average linkage and Euclidean distance metric; for example TIGR MeV (Multiple Experimental Viewer) (the Institute for Genomic Research) for clustering visualization. These data analyses will generate binding data sets that can be compared from array to array; sequence-specific binding information will be further analyzed and extracted using the PepChip Pro software.

Figure 7:
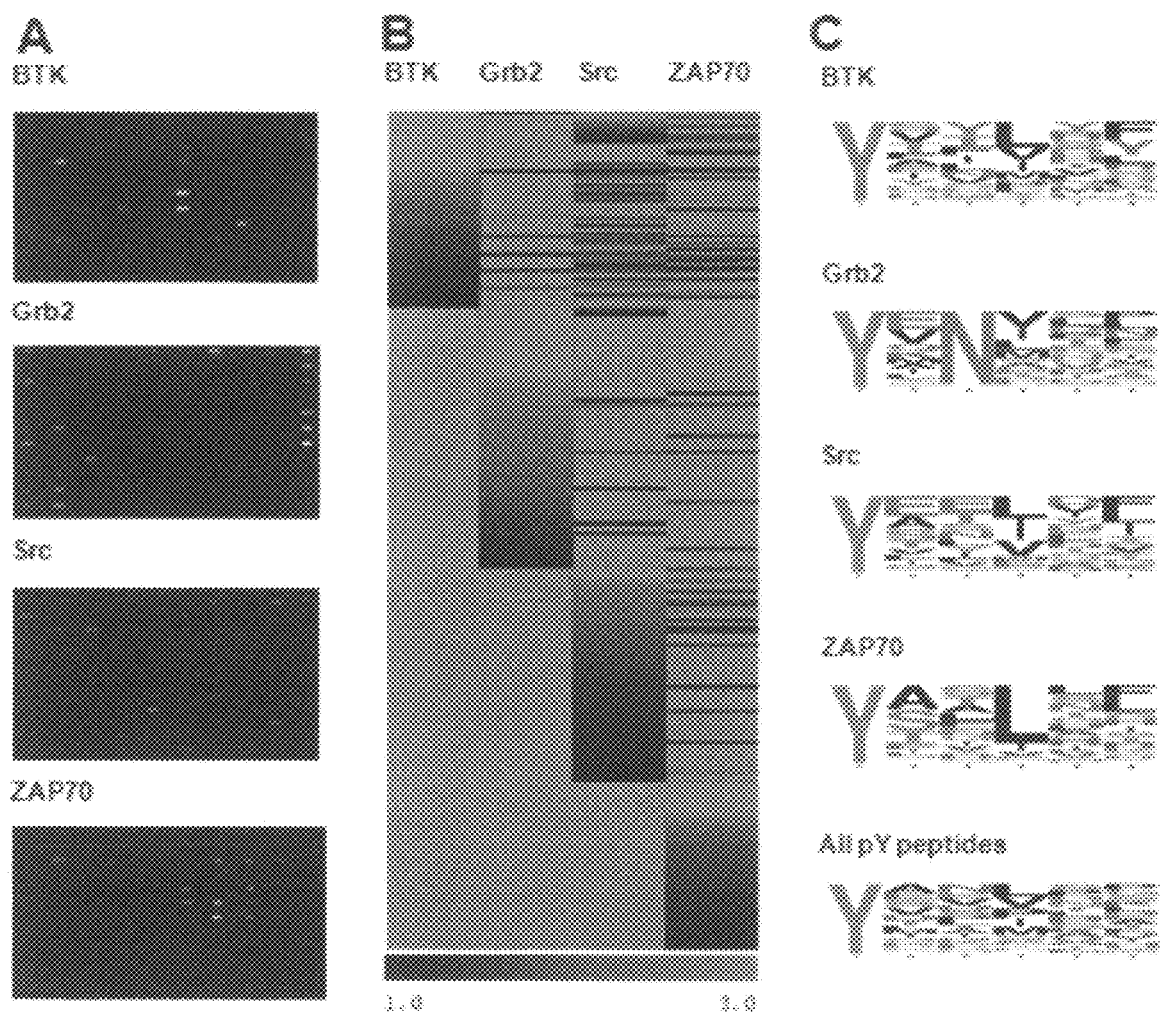
FIG. 7A-C—Binding profiles of 4 SH2 proteins
Figure 9:
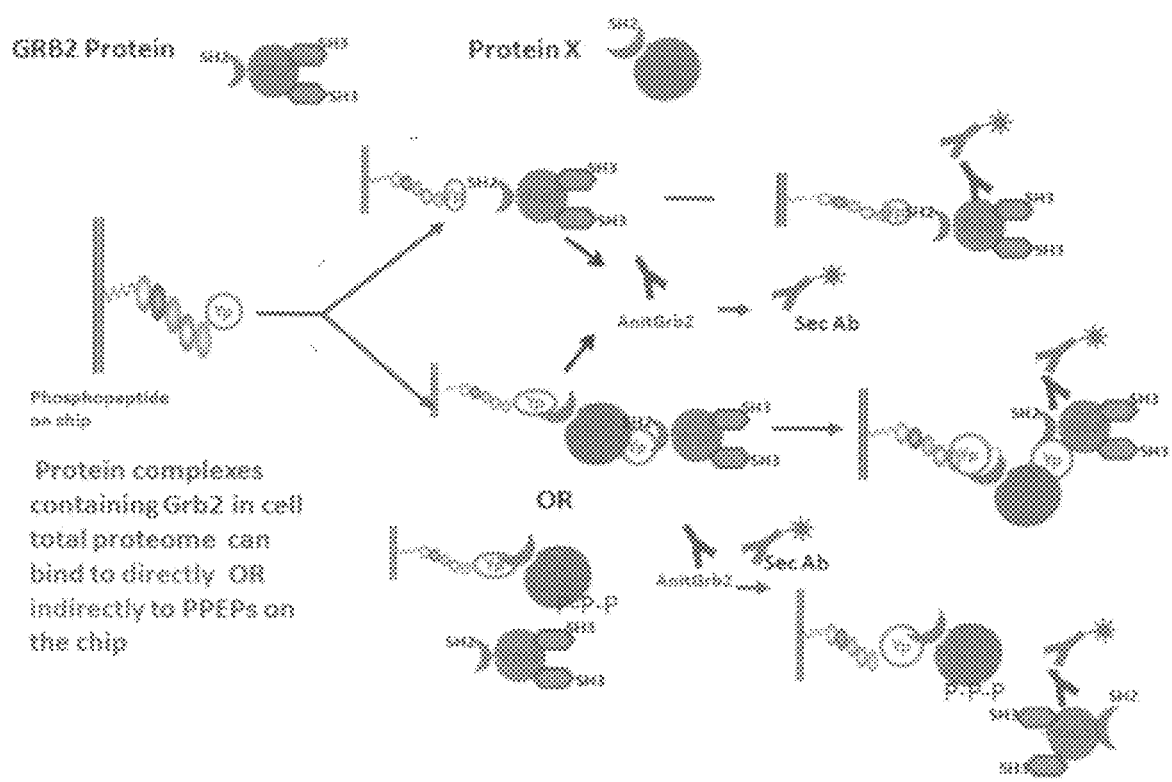
FIG. 9—Diagram of indirect and direct binding of Grb2.

FIG. 7A shows the binding profiles of 4 SH2 proteins on the same region of SH2-PPEP microarray, while FIG. 7B is a heat map of binding intensities of 4 SH2 proteins to related PPEPs. The binding signals were normalized into Z values. The PPEPs with Z values ranked from 1.0-3.0 were selected to plot the heat map. FIG. 7C displays the consensus sequences of binding sequences of 4 SH2 proteins. The consensus sequences were generated by using Weblogo.

The present invention relates to methods for detecting phosphoproteins on peptide microarrays. The phosphoproteins in a cell may be detected by making a microarray containing peptides that bind phosphoproteins, lysing cells and collecting the proteins from the cells, covering the microarray with the proteins and detecting the phosphoproteins.

The present invention relates to methods for differential detection of phosphoprotein expression in cancerous and non-cancerous cells. The differential expression of the phosphoproteins in cancerous and non-cancerous cells may be determined by making a microarray containing peptides that bind phosphoproteins and lysing the cancerous cells and collecting proteins from the cells and the covering the microarray with the proteins and detecting the phosphoproteins from the cancerous cells. The same method can be used for non-cancerous cells: lysing the non-cancerous cells, collecting proteins from these cells and the covering the microarray with the proteins and detecting the phosphoproteins from the non-cancerous cells and comparing the relative expression of these proteins in cancerous and non-cancerous cells.

The present invention relates to methods for detecting phosphoproteins on peptide microarrays. The phosphoproteins in a cell may be detected by making a microarray containing peptides that bind phosphoproteins, lysing cells and collecting the proteins from the cells, covering the microarray with the proteins and detecting the phosphoproteins.

The present invention relates to methods for differential detection of phosphoprotein expression in cancerous and non-cancerous cells. The differential expression of the phosphoproteins in cancerous and non-cancerous cells may be determined by making a microarray containing peptides that bind phosphoproteins and lysing the cancerous cells and collecting proteins from the cells and the covering the microarray with the proteins and detecting the phosphoproteins from the cancerous cells. The same method can be used for non-cancerous cells: lysing the non-cancerous cells, collecting proteins from these cells and the covering the microarray with the proteins and detecting the phosphoproteins from the non-cancerous cells and comparing the relative expression of these proteins in cancerous and non-cancerous cells.

Kinases have become a class of molecules that are being pursued as drug targets. In particular kinase inhibitors have been developed to interfere with kinases in hopes of developing cancer drugs. There are several types of kinase targets that could be subjected to drug treatment to prevent or ameliorate certain cancers. First, there are kinase targets that have become impervious to normal regulatory mechanisms following genetic mutation or translocation. These kinases have transforming capacity and thus are considered to be oncogenic. For example PI3KCA is frequently mutated in numerous cancers and the V600E mutation, located in the activation loop of BRAF, which has been implicated in the development of carcinomas of the skin, ovary, thyroid, colon and pancreas. The V617F activating mutation in the auto-inhibitory pseudokinase domain of JAK2 is frequently found in polycthaemia vera, essential thrombocythaemia andidiopathic myelofibrosis and has stimulated the rapid progression of several JAK2 inhibitors into clinical studies. Another class of kinase targets includes those kinases where the inhibition of the kinase results in a synthetic lethal phenotype when paired with another non-lethal mutation in the particular pathology of the tumor cell. Although not oncogenic and rarely mutated in cancer, these kinases are preferably required for the survival and/or proliferation of cancer cells and may be located in key signaling pathways located downstream of transforming oncogenes. Examples include MEK1 and MEK2 (also known as MAP2K1 and MAP2K2), mTOR (also known as FPAR1) located in the PI3K-Akt signaling system and the ribosomal 56 kinase (RSK) which is downstream of the fibroblast growth factor (FGF). A third class of kinase targets are expressed in the tumor or in the surrounding tissues and are required for different stages of tumor formation and maintenance in the human host. Examples include NTRK2 which is essential for allowing some cells to survive detachment and may also be required for tumor cell metastasis, vascular endothelial growth factor receptor (VEGFR) and FGFR kinases which are important in developing and sustaining tumor blood supply and M2 splice isoform of pyruvate kinase which is required for the tumorigenic switch to aerobic glycolysis that occurs in cancer cells. Figure X shows a map of a SH protein network.

Kinase inhibitors have been developed to interfere with the normal function of the target kinases. Most kinase inhibitors thus far developed are ATP competitive and present one to three hydrogens bonds to the amino acids located in the hinge region of the target kinase, thereby mimicking the hydrogen bonds that are normally formed by the adenine ring of ATP. There are several inhibitor types that can be exploited as cancer drugs: Type 1 inhibitors, Type 2 inhibitors, allosteric inhibitors and covalent inhibitors. Type 1 inhibitors recognize the active conformation of the kinase which is conducive to phosphotransfer. Type 1 inhibitors typically consist of a heterocyclic ring system that occupies the purine binding site. Type 2 inhibitors recognize the inactive conformation of the kinase. Imatinib and nilotinib are inhibitors of platelet-derived growth factor receptor (PDGFR), sorafenib is an inhibitor of KIT, Raf and PDGFR. Allosteric inhibitors bind outside the ATP-binding sites. These inhibitors tend to exhibit the highest degree of kinase selectivity because they exploit binding sites and regulatory mechanisms that are unique to a particular kinase. CI-1040 is an allosteric inhibitor of MEK1 and MEK2 by occupying a site adjacent to the kinase ATP binding site. Other examples include GNF2, Akt-l-1, IKK, BMS-34551. Covalent inhibitors are capable of forming an irreversible covalent bond to the kinase active site frequently reacting with a nucleophilic cysteine residue. These inhibitors are often designed by appending an electrophile to the well-characterized EGFR-selective 4-anilinoquinazoline and 4-anilinoquinoline-3-carbonitrile scaffolds (Zhang et al. (2009) Targeting cancer with small molecule kinase inhibitors, Nature Reviews (9): 28-37).

The present invention relates to methods for differential detection of phosphoprotein expression in cancer cells treated with a kinase inhibitor and untreated cancerous cells. The differential expression of the phosphoproteins in cancer cells treated with a kinase inhibitor and untreated cancerous cells may be determined by making a microarray containing peptides that bind phosphoproteins and lysing the cancer cells treated with a kinase inhibitor and collecting proteins from the cells and introducing the proteins to the microarray and detecting the phosphoproteins from the kinase inhibitor treated cancer cells. The same method can be used for untreated cancerous cells (lysing the untreated cancerous cells, collecting proteins from these cells and the covering the microarray with the proteins and detecting the phosphoproteins from the untreated cancerous cells and comparing the relative expression of these proteins in kinase inhibitor treated cancer cells and untreated cancerous cells.

Figure 17:
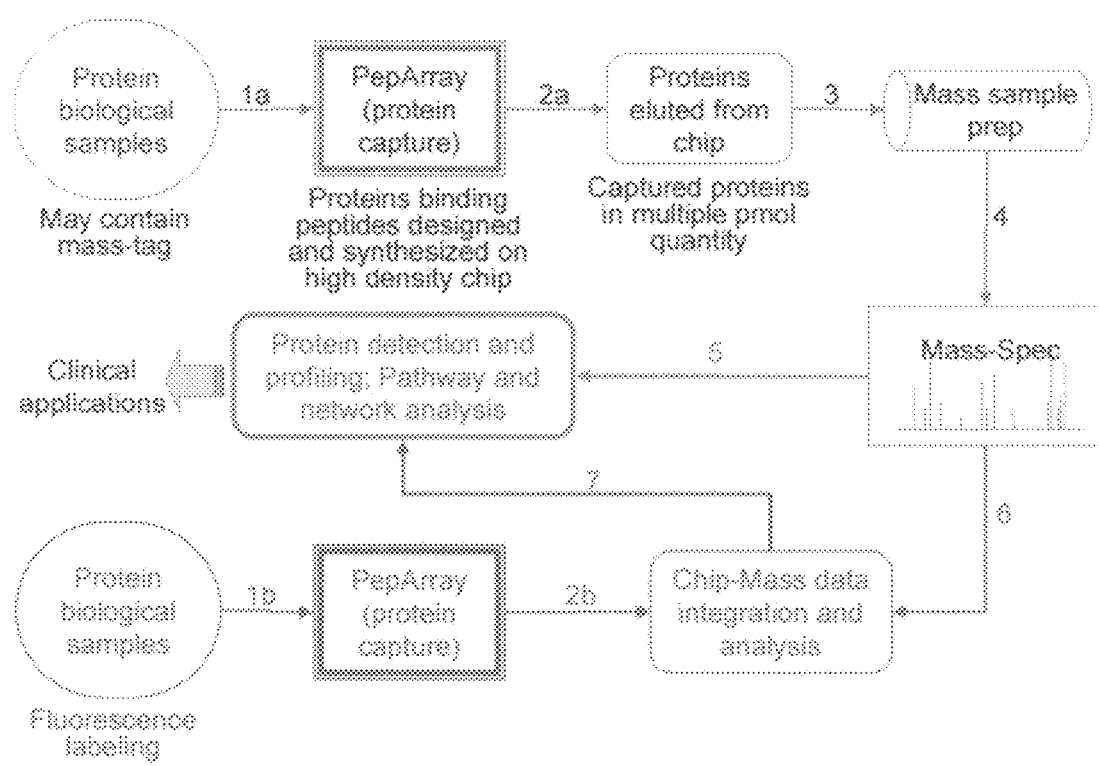
FIG. 17 is a schematic diagram that shows how captured proteins can be analyzed by mass spectroscopy.

In addition to profiling the relative presence of proteins, including phosphoproteins in cell lysates, the microarrays of the present invention may also be used to characterize the captured proteins by other analytical techniques. FIG. 17 is a schematic diagram that shows how captured proteins can be analyzed by mass spectroscopy. Chip-Mass proteomics technology permits an increasing number of proteins (target proteins), especially low abundance proteins, to be captured by binding to peptides (peptide as used herein includes but is not limited to amide bond linked oligomers of natural amino acids, modified amino acids (peptidomimetics) such as peptoids, or N-substituted glycines oligomers), on microarray surface. Protein binding peptides are synthesized on chip so that specific proteins in samples can be enriched by capturing on chip surface while undesirable proteins are washed away. The bound proteins can be reversibly detached (eluted) from the chip and the resultant protein solution contains proteins of interest at multiple-fold concentrations compared to in vivo and thus better detected and analyzed by mass spectrometry which provides protein identification. There are large numbers of natural peptides which are protein binders (ligands), such as phosphopeptides, specific protein domain binding peptides, or inhibitors of protein activities. New protein binding peptides can be discovered and synthetically created providing an essentially limitless number of peptides for capture. Systematic development of protein binding peptides for biologically important proteins based on their common binding properties lead to the collection of protein binding peptides that would have the capacity of protein capture on a proteome scale.

The 4 k chip, describe above, can achieve multiple fmol per protein quantity for the mass analysis. If the mass experiments require additional materials, a larger chip with greater capacity or multiple runs of binding and washing off the proteins from the chip can be utilized.

FIG. 17 describes the steps of characterizing proteins via chip-mass proteomics. In step a, a protein sample (mixture of proteins of biological or synthetic origin) is applied to the microarray for protein capture by using target-specific binding peptides (and peptidomimetics) synthesized on chip. Protein capture is optimized for binding conditions and the target proteins are enriched on chip. Then, target proteins are eluted from chip and recovered in solution for protein identification by mass spec analysis. The eluted target proteins are treated for salt removal to become compatible for mass instrument. Mass spectra of the target proteins are obtained. In one preferred embodiment silver-stained gel pieces containing proteins of interest can be destained and digested in-gel with trypsin. The peptides can be extracted and analyzed by Nano-LC-MS/MS with on-line desalting.

Mass data analysis programs are used to produce protein IDs and further analysis will be correlated with cancer biology and systems biology. Mass spec and Chip data of the same protein sample can be integrated to demonstrate the advantage being specific, quantitative, and reproducible and will be continuously optimized to provide the information required by clinical applications. The protein sample may contain fluorescence labels and the capture on the microarray can be imaged. Since peptides on chip are correlated with the known target proteins, the binding shown by fluorescence signal intensities produces quantitative information of the proteins captured. This information and the protein ID obtained from mass spec analysis can be integrated.

One particular application area for the peptide microarray is targeted capture of serine and cysteine peptidases in gliomas for subsequent quantitative proteomics analysis using subsets of serine and/or cysteine peptidases. The designed microarrays for protein capture include cysteine peptidases: C1 (papain family) including all cathepsins. Altogether 19 members in human.; family C2 (calpain family), originally named "calcium-dependent neutral peptidases" as they were found in the brain, 15 members in total in human; C14 (caspase family), including all caspases that control the apoptosis cascade. The serine peptidase family S9 (prolyl oligopeptidase family) peptidases is also of interest. The active site motif is GGSXGGLL where X is typically Asn or Ala (S9A subfamily), GWSYGGY (S9B subfamily), GGSYGG (S9C subfamily) and GGH-SYGAFMT (S9D subfamily). This family contains many of the unknown serine peptidases such as hypothetical protein-flj40219, flj37464, flj33678, dipeptidylpeptidase homologue DPP6, C14orf29 protein, FLJ1 putative peptidase etc., which have not been well studied due to lack of reagents (e.g. lack of antibodies).

Another area of particular interest is peptidases. Peptidases (previously called proteases) are one of the largest families of enzyme proteins in human, over 500 are estimated. The function of peptidases is to cleave a peptide bond (—C(O)—HNR—, the middle thicker bond) as required by protein activation, degradation, and other kinds of processing in cells, virus, toxins, etc. Cysteine and serine proteases are two important families of the enzymes, which also play a role in brain tumor migration and metastasis. Therefore, the expression of peptidases and their mutations often could be associated with perturbation of normal cellular processes or mechanisms of tumor genesis. Peptidases are not natural binders of the substrate peptides but several groups of molecules could be candidate molecules from which the protease activities are eliminated and the binding of the proteins to peptides on a microarray can be optimized. Examples of these groups include peptidase substrates (hundreds of these peptides are available in literature and web sources), small molecule inhibitors (some of these are peptides and others are small organic molecules) and protein inhibitors (such as TRIAP1 is a TP53-regulated inhibitor of apoptosis 1 for metallopeptidases). Captopril is a small dipeptide inhibitor for angiontension convertion enzyme I. Its binding to the site of the target protein in the crystal structure of the complex is an example about the inhibitors are convertible to capture molecules when the inhibitor molecules are synthesized on surface.

The greatest difficulties encountered in protein assays result from problems related to protein surface adhesion or protein stability. Therefore the surface chemistry, blocking procedures, and experimental conditions should be tailored to maintain protein stability. One method for keeping the peptides stable is to use well-derivatized neutral alkyl-oligoethylene glycosyl-containing surfaces to carry out peptide synthesis. Additionally, a blocking solution cocktail containing non-fat dry milk, BSA, detergents, and buffer solution gives reproducibly low background. In one embodiment of the methods of the present invention the peptide array assays use solution circulation at a suitable flow rate which is usually about 20-100 µL/min. Protein concentration may also be important since maintaining the protein in its soluble form is preferable; proteins tend to precipitate at high concentrations, causing clotting problems. Temperature is also important for the maintenance of protein stability. The bottom layer of one type of microfluidic chip is Si which is highly thermal-conductive. Temperature regulation may be achieved contacting the chip surface with a heating/cooling device. Protein sample precipitation may be an issue for microfluidic chips, which have narrow (30 µm) flow channels. This problem can be effectively avoided by lowering the protein concentration, use low temperature, centrifuging the sample, using a bi-directional peristaltic pump, using a slower flow rate, shortening experimental time, or some combination of these adjustments.

EXAMPLES

Example 1

Microarray Chip Design

Phospho-peptide microarray chips were designed using Peparray pro program (Li, T., Zuo, Z., Zhu, Q., Hong, A., Zhou, X., Gao, X. (2009) Web-based design of peptide microarrays using mPepArray Pro. Invited review in "Peptide Microarrays" in Methods and Protocols. 570, 391-402. Ed. Cretich, M). The SH2 protein array used a total of 1226 tyrosine phosphomotifs (PPEPs) representing phosphomotifs from 423 proteins mediating 2455 interaction from PepCyber:P~PEP (Gong, W., Zhou, D., Ren, Y., Wang, Y., Zuo, Z., Shen, Y., Xiao, F., Zhu, Q., Hong, A., Zhou, Z., Gao, X., and Li, T. (2008) PepCyber:P~PEP: A database of human protein-protein interactions mediated by phosphoprotein binding domains. Nucleic Acids Res. 36, D679-D683). The RTK pathway array peptides were collected by mining phosphoprotein data from various protein databases (PepCyber, Phopho.ELM, PhosphoSite etc.) containing a total number of 191 proteins with 786 tyrosine phosphor-motifs. These include 49 RTKs, 28 cytoplasmic TKs, 32 signaling adaptor proteins and 82 other downstream signaling proteins Example 2

Phosphopeptide Array Chips (PPEP Array Chip)

Phosphopeptide array chips (PPEP array chip) were made by in situ synthesis on microfluidic microchips. Thousands of PPEPs were designed based on phosphorylation or signaling pathway information which enabled the probing for proteins which mediate signaling transduction pathways, such as kinases related SRC, PLCG2, PIK3R1, adaptors LCK, CSK, FYN, GRB2, GRB10, transcription activity factors STATs and phosphotases SHP1 and SHP2. Each pY peptide was synthesized in triplicate. Control sequences were synthesized where the tyrosine phosphomotifs (pY) was replaced by an alanine (A). Receptor tyrosine kinase (RTK) PPEPs were created to cover 52 of the 58 human RTK using 644 PPEPs, which are also known phosphoprotein binding domain (PPBD) motifs. These are probes that monitor cellular tyrosine kinase inhibitor responses, tyrosine phosphorylation activities.

Example 3 pYPeptide-GRB2 Binding Assay and Data Processing

The PPEP array chip surfaces were subjected to stringent pretreatment for uniform, selective cell lysate protein binding. After equilibration with protein binding buffer (PBB), either recombinant protein (200 ng/mL) or cell lysate (1 mg/mL) extracted from cancer cells was used for overnight binding at 4° C. This was followed by primary antibody incubation (1 hr for recombinant protein at RT; overnight incubation of cell lysate) and secondary antibody binding (1 hr at RT) with washing (1 hour with PBB) between each step to remove unbound reagents. The chip was mounted on a chip holder and scanned using the microchip array scanner Anon GenePix 4400A (Molecular devices) using the Genepixpro7 software.

A software program (Array-Pro Analyzer) was used and the numerical pixel density values were obtained as text file (output data). The pixel data is merged with layout file using an In-house micro-array analysis program (macros in excel) where the data is background subtracted. Based on several other parameters the significant data values are reported detectables.

The data was further analyzed for the biology of each protein that represents the phosphomotifs (pathway analysis, GO term analysis etc).

Example 4

Cell Lysis, Immunoprecipitation and Western Analysis

Cells containing recombinant SRC, Grb2, BTK and ZAP70 were washed 4 times in cold PBS and lysed in 1-2 mL of lysis buffer containing 20 mM Tris (pH 8), 1% TX-100, 10% glycerol, 137 mM NaCl, 5 mM sodium orthovanadate along with 1% phosphatase inhibitor cocktail and 1% protease inhibitor cocktail (Roche) for 1 hour at 4 degree C. The cells were centrifuged at 14K RPM for 20 min to remove the DNA and cellular debris. The protein supernatant was collected and filtered through a 0.2 um filter and the filtered protein lysate was collected and aliquoted in to 500 uL volume and stored at minus 80 degree deep freezer. The concentration was determined using DC assay kit (BioRad) based on Lowry method.

About 500 μg of total protein was incubated with the appropriate phosphospecific antibody for one hour at 4° C. Protein SEPHAROSE A/G beads (Dyna beads from invitrogen) were used to collect the antigen antibody complexes for about one hour. Immunoprecipitates were then washed three times with cold lysis buffer. Proteins in the IP complex were analyzed by resolving in 8-12% PAGE gels and blotting with appropriate antibody. Signals were detected using the infra-red dye conjugated secondary antibodies and signals detected using Odyssey IR image analyzer (LICOR Biosciences).

Based on the analysis of over 100 PPEPs with Grb2 SH2 high binding signals, it was determined that for GRB2 SH2 domain the binding motif the consensus of phosphopeptides is pY-E/V/Q/K-N-V/I/L. This binding motif is similar with the reported (pY-E/Q-N-ψ (ψ represents a hydrophobic residues). Based on our results and those from literature, the asparigine residue at P+2 is essential for Grb2 SH2 binding, whereas selectivity at P+1 and P+3 is apparent, but less stringent. These three amino acid positions at the C-terminal of pY are sufficient for optimal Grb2 SH2 binding with high affinity and specificity. The peptide signature for other proteins (SRC, BTK and ZAP70) also confirms results from previous studies (Huang H, Li L, Wu C, Schibli D, Colwill K, Ma 5, Li C, Roy P, Ho K, Songyang Z, Pawson T, Gao Y, Li S S. (2008) Defining the specificity space of the human SRC homology 2 domain. Mol Cell Proteomics. 7(4):768-841). Using μParaflo® PepArray Microchip system, we not only detected experimentally proven interactions but also validated many predicted interactions.

Example 5

Phosphopeptide Binding of Protein Complexes in Cells

Figure 10:
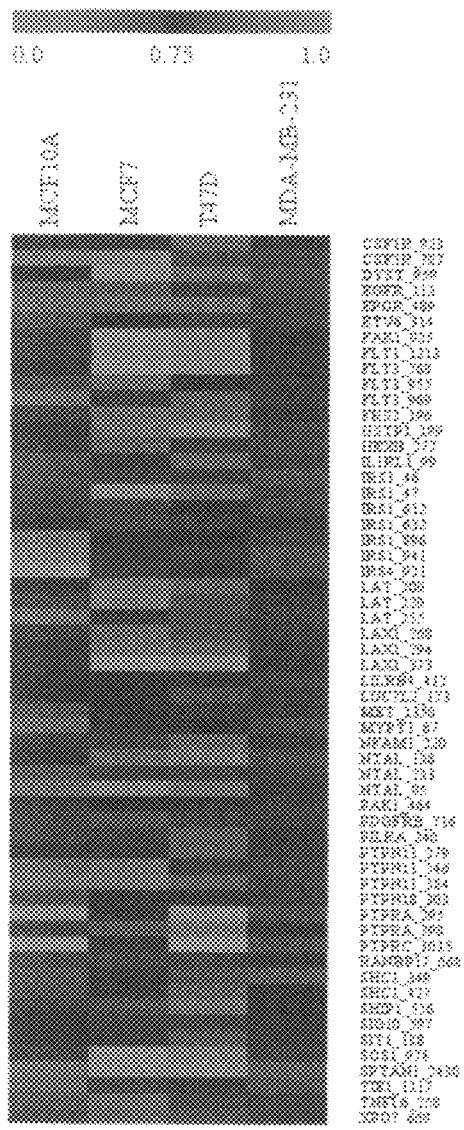
FIG. 10—Heat map from breast cells show increasing signals for detected proteins in T47D and MCF7 tumor cells.
Figure 13:
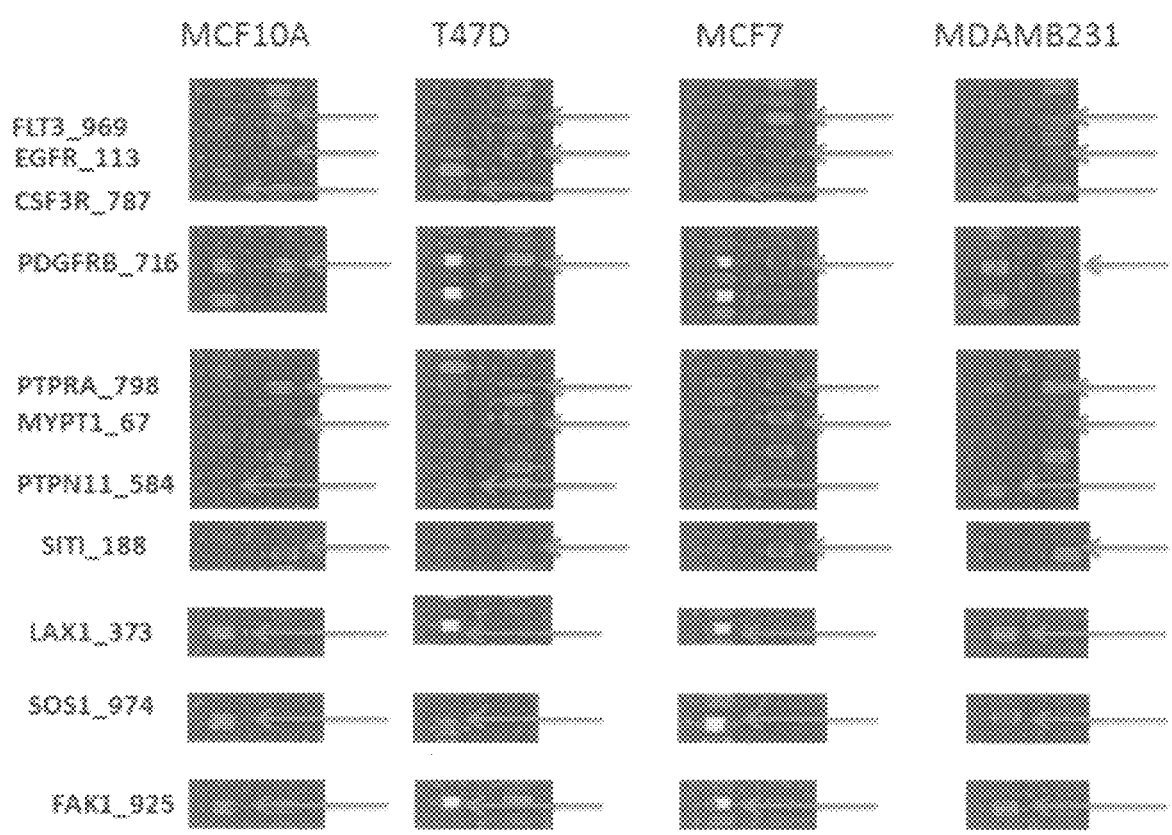
FIG. 13—GRB2-RTK pY proteome interaction networks in breast cancer cells as shown on microarray.
Figure 14:
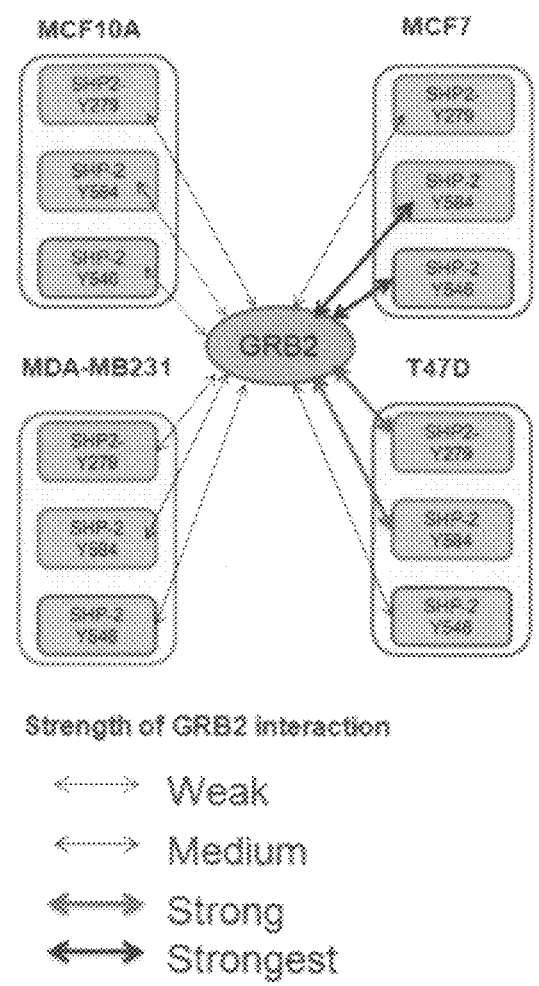
FIG. 14—Diagram of interaction of GRB2 with all three pY motifs are upregulated in tumor cells (MCF7 and T47D) but significantly down-regulated in MCF10A and MDA-MB231 cell.

Total protein was isolated from cultured T-47D (ATCC Accession No. HTB-133) breast ductal carcinoma and MCF7 (ATCC Accession No. HTB-22) breast adenocarcinoma and MCF10A (ATCC Accession No. CRL 10317) breast epithelial and MDA-MB231 (ATCC Accession No. HTB-26) breast cells and was passed over the chip through microfluidics based circulation at 4 degree C. for overnight. Antibody based detection was used to identify the protein of interest on these complexes. Based on in vivo substrate affinity of a specific phosphoprotein with its binding protein, in vivo protein complexes bound to phospho-peptides (pY) on the chip from the pool of non-denatured total proteins isolated from cells could be detected. FIG. 10 shows the heat map from breast cells show increasing signals for detected proteins in T-47D and MCF7 tumor cells. FIG. 14 shows the interaction of GRB2 with all three pY motifs are upregulated in tumor cells (MCF7 and T47D) but significantly downregulated in MCF10A and MDA-MB231 cells. The interaction dynamics as measured by the amount of GRB2 bound to the phospho-motif was sufficient to distinguish the cellular signature of a non-tumorogenic mammary epithelial cell (MCF10A) from breast cancer cells (MCF7, T47D and MDAMB231). These interaction signatures are diagnostic for each cancer type we analyzed. A generic downregulation of phospho-proteome-GRB2 interaction network in the metastatic tumor cell MDA-MB-231 was observed compared to tumorogenic MCF7 and T47D cells.

Example 6

Protein Capture and Mass Analysis

Samples of three SH2 proteins (PI3K/P85α two SH2 domain; PLC-γ, and GRB2), each SH2 protein contained a GST fusion tag and was complexed with mouse IgG which was conjugated with HiLyte Plus 647 fluorescence dye (Abcam). 100 uL of the three protein solution (each at 50 ug/mL) was used. The binding array images were acquired using GenPix 4000B laser scanner. The gel used ½ of the elution solution. Silver-stained gel pieces were destained and digested in-gel with 200 ng modified trypsin (sequencing grade, Promega) for 18 hrs at 37 C. Resulting peptides were extracted and analyzed by Nano-LC-MS/MS with on-line desalting. The Nano-LC system consisted of a Famos® autosampler, Ultimate® Nano-LC module and a Switchos® pre-column switching device (LC-Packings/Dionex Corp., Sunnyvale Calif.) used with a 75-micron ID C18-column as the analytical column and a 0.3×5 mm C18 desalting column (both from LC-Packings) plumbed on the Switchos® for on-line desalting. Samples were injected using the "microliter pickup" method allowing all of the liquid removed from the sample vial to be sandwich-loaded into the sample loop, then injected onto the desalting column at 40 microliters/minute in 2% acetonitrile/water containing 0.01% TFA. The separation column was operated at approximately 200 nL/min flow rate, equilibrated in 5% acetonitrile prior to injection and eluted with a linear acetonitrile gradient to 30 or 40% followed by a wash at 65% acetonitrile (containing 0.01% TFA) and re-equilibration in initial conditions. Column effluent was introduced to the mass spectrometer using the ThermoFinnigan NanoSpray source fitted with a spray tip from New Objective (New York). Electrospray ion trap mass spectrometry was performed on a linear ion-trap mass spectrometer (LTQ, Thermo, San Jose, Calif.) Typical settings were: spray-tip voltage 2000, inlet tube temperature 120° C., tube voltage 100V, tube lens offset 20V. Typically one survey scan was followed by three data-dependent MS/MS scans, using CID (collision-induced dissociation) to induce fragmentation. Proteins were identified by database searching of the fragment spectra against the NCBI non-redundant protein database using Mascot (Matrix Science, London, UK) or Sequest (Thermo, San Jose, Calif.).

Figure 18:
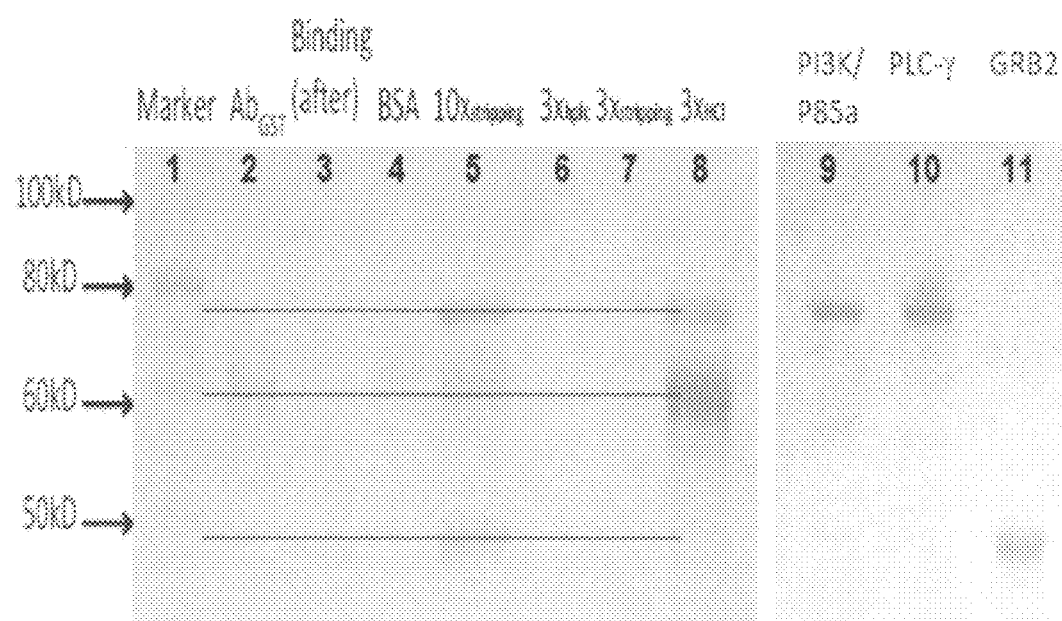

FIG. 18 shows the results of the capture experiment. Lane 1: Molecular weight marker. Lane 2: Anti-GST antibody (60 k band is likely due to keratins 1, 9, 2, and 10 by mass spec analysis). Lane 3: Capture protein binding solution collected after the PepArray binding experiment. Lane 4: BSA only. Lane 5: Elution solution was strip buffer (2% SDS, 50 mM Tris, 100 ⍰M 2-mercaptaethanol, 0.1% triton, pH5.8), binding and elution was repeated 10 times (10×). Three gel bands were clearly observed, which were ~75 k, ~60 k (broad), and ~48 k. A very faint band (not seen in the figure) was ~30 k. Lane 6: Elution solution was 0.1% trifluoroacetic acid (TFA) in $H_2O$:ACN=8:2 (vol), elution was repeated 3×; Lane 7: Elution was 3× strip buffer (see lane 5); Lane 8: Elution solution was 10 mM HCl which showed increased presence of the broad 60 k keratins band and decreasing 48 k band. Mass analysis was carried out. The ~75 k band ID indicates PI3K (score=610, 20 matches) and PLC-gamma (score=175, 3 matches); the ~65 k band ID indicates mainly keratins 1, 9, 2, and 10, likely due to environmental contamination at some point of the process; the ~48 k band ID indicates GRB2 (score=495, 40 matches) along with traces of keratins; a much weaker ~30 k band ID (extremely faint) indicates low levels of GRB2 and PI3K. Mass analyses are consistent with the detection of the three SH2 proteins. These results demonstrate microarray-based protein capture for use in multiple protein analysis.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

The invention claimed is:

1. A method for differential detection of phosphoprotein expression in cancerous and non-cancerous cells comprising:
   a) making a microarray containing peptides that bind phosphoproteins;
   b) lysing the cancerous cells and collecting proteins from the cells;
   c) binding the phosphoproteins with peptides on the microarray;
   d) detecting the phosphoproteins; and
   e) repeating steps b-d using the non-cancerous cells and comparing the results.

* * * * *